(12) United States Patent
Sakata et al.

(10) Patent No.: US 8,846,089 B2
(45) Date of Patent: Sep. 30, 2014

(54) SUGAR-COATED PREPARATION AND PRODUCTION METHOD FOR THE SAME

(75) Inventors: Yukoh Sakata, Akitakata (JP); Masaharu Higuchi, Akitakata (JP)

(73) Assignee: Wakunaga Pharmaceutical Co., Ltd., Osaka-Shi (JP)

( * ) Notice: Subject to any disclaimer, the term of this patent is extended or adjusted under 35 U.S.C. 154(b) by 0 days.

(21) Appl. No.: 13/483,595

(22) Filed: May 30, 2012

(65) Prior Publication Data

US 2012/0308656 A1 Dec. 6, 2012

(30) Foreign Application Priority Data

Jun. 3, 2011 (JP) ................................. 2011-125729

(51) Int. Cl.
 *A61K 9/36* (2006.01)
 *A61K 9/14* (2006.01)
 *A61K 47/32* (2006.01)
 *A61K 9/28* (2006.01)

(52) U.S. Cl.
 CPC ............... *A61K 9/2826* (2013.01); *A61K 9/284* (2013.01); *A61K 9/2893* (2013.01)
 USPC .......................... 424/479; 424/493; 514/772.2

(58) Field of Classification Search
 None
 See application file for complete search history.

(56) References Cited

U.S. PATENT DOCUMENTS

2005/0271724 A1* 12/2005 Clark et al. ................... 424/472

FOREIGN PATENT DOCUMENTS

| JP | 3507211 B | 1/1997 |
|---|---|---|
| JP | 2002-179559 A | 6/2002 |
| JP | 2003-155232 A | 5/2003 |
| JP | 4391732 B | 4/2004 |
| JP | 2004-137224 A | 5/2004 |
| JP | 2004-155656 A | 6/2004 |
| JP | 2004-155775 A | 6/2004 |
| JP | 2008-201711 A | 9/2008 |
| JP | 2008-260778 A | 10/2008 |
| JP | 2009-073814 A | 4/2009 |

OTHER PUBLICATIONS

A raw machine translation, dated Apr. 3, 2013, has been provided for JP2004-107282 which was cited in the IDS.*

* cited by examiner

*Primary Examiner* — Bethany Barham
*Assistant Examiner* — Jessica Worsham
(74) *Attorney, Agent, or Firm* — Leason Ellis LLP.

(57) ABSTRACT

A method is provided for producing a sugar-coated preparation including a solid composition containing a pharmacologically active ingredient and a sugar coating layer. The method comprises a step of forming the sugar coating layer with a sugar coating composition containing one or more sugar-alcohols selected from the group consisting of mannitol and erythritol and a polyvinyl alcohol-based resin. The sugar-coated preparation includes a solid composition containing a pharmacologically active ingredient and a sugar coating layer, wherein the sugar coating layer is made of a sugar coating composition containing one or more sugar-alcohols selected from the group consisting of mannitol and erythritol and a polyvinyl alcohol-based resin.

10 Claims, 1 Drawing Sheet

SUGAR-COATED PREPARATION AND PRODUCTION METHOD FOR THE SAME

CROSS-REFERENCE TO RELATED PATENT APPLICATIONS

This application claims the benefit of Japanese Patent Application No. 2011-125729, filed Jun. 3, 2011, which is incorporated by reference herein.

FIELD OF THE INVENTION

The present invention relates to a sugar-coated preparation including a sugar-coating layer which is formed by a specific sugar coating composition, and a production method for the sugar-coated preparation. More particularly, the present invention relates to a sugar-coated preparation, having a superior ability to mask unpleasant odor, superior moisture resistance and is provided with a thin sugar layer made by a simple production process, and to a production method for the sugar-coated preparation.

BACKGROUND ART OF THE INVENTION

Tablets refer to a product form obtained by compressing a powder or granules and the like into a fixed shape. Since the tablets can be easily transported and enable a fixed dose to be taken easily, the tablets are the most commonly used drug form in fields such as pharmaceuticals, quasi drugs, cosmetics, functional foods and health foods. Tablets come in various types, such as uncoated tablets, coated tablets, chewable tablets, orally disintegrating tablets or effervescent tablets, depending on the content thereof and purpose of use. The tablets in various type are used in various fields.

Coated tablets are obtained by uniformly forming a coating on the surface of uncoated tablets for the purpose of masking the taste or odor of the contents of the tablets, preventing degeneration and deterioration of the components caused by humidity and the like, and improving appearance and sensation to the tongue. Coated tablets can be roughly divided into sugar-coated tablets having a coating layer mainly containing a sugar as a coating film, and film-coated tablets having a coating layer mainly containing a water-soluble polymer or a poorly water-soluble polymer as a coating film.

The sugar-coated tablets offer the advantages of effectively masking odors, having high moisture resistance and having an attractive appearance. Conversely, the sugar-coated tables have the disadvantage of having a complex production procedure since they are coated by undergoing repeated application of liquid, spreading and drying using a large amount of a sugar coating liquid containing mainly sugar. In addition, they also have disadvantages with respect to susceptibility to cracking and chipping, having a high calorie content and imparting a high moisture content to the resulting preparation.

On the other hand, since film-coated tablets can be coated using only a small amount of coating liquid, the production procedure thereof is less complex. In addition, film-coated tablets also offer the advantages of containing fewer calories and undergoing little cracking or chipping. Conversely, film-coated tablets have disadvantages with respect to low moisture resistance and little ability to mask unpleasant odors. In this manner, sugar-coated tablets and film-coated tablets exhibit opposite properties.

Therefore, thin layer sugar-coated tablets have been developed that maintain a strong masking ability with respect to odors possessed by sugar-coated tablets while having high moisture resistance and a small coated amount. Thin layer sugar-coated tablets are normally produced by sequentially coating uncoated tablets with a protective coating layer, sub-coating layer, coloring layer and polishing layer. Each of these layers is formed by a syrup containing white sugar as a base thereof, and gelatin or powdered gum arabic as a binder. Otherwise, it is also possible to form these layers by further spraying a powder such as talc, precipitated calcium carbonate, calcium phosphate or calcium sulfate as necessary. Furthermore, it is also possible to form these layers by using a suspended composition in which the powder is suspended in the syrup. The protective coating layer that coats the uncoated tablet is formed to inhibit migration of moisture content contained in the sugar coating liquid or syrup liquid used in the sub-coating layer and coloring layer to the inside of the tablet. The sub-coating layer formed on the upper surface of the protective coating layer is formed to impart roundness to the central tablet and enhance coating strength. The coloring layer is formed to inhibit air permeability and moisture permeability by forming fine crystals of a sugar component. Finally, the tablet surface is polished by forming the polishing layer. Although the coating layer of thin layer sugar-coated tablets is thinner than that of sugar-coated tablets, since these tablets are produced by coating with numerous layers in this manner, the complexity of the production procedure has been considered to be a problem.

Development has previously been carried out on coated tablets having superior masking ability and the ability to prevent degeneration and deterioration of their contents while also being able to be produced more easily.

For example, Japanese Patent Application Laid-Open (kokai) No. 2002-179559 discloses a thin layer sugar-coated tablet which is coated with 5% by mass to 60% by mass of a sugar coating liquid containing a sugar, a vehicle and a binder, relative to the total weight of the uncoated tablet, in order to mask unpleasant odors, prevent the occurrence of whiskers, stabilize a drug that decomposes at a high moisture content and reduce the size of the tablet, and a production method thereof.

In addition, Japanese Patent Application Laid-Open (kokai) No. 2003-155232 discloses a solid preparation which contains L-cysteine and has a reduced level of unpleasant odor by incorporating L-cysteine using a dry method, and a production method thereof. Japanese Patent Application Laid-Open (kokai) No. 2004-155656 discloses a sugar-coated tablet including a coating layer, which contains a powder, a binder and less than 10% by mass of a sugar, between an uncoated tablet or film-coated tablet and a sugar coating layer, in order to enhance masking effects on odor, color, taste and the like as well as reduce size and shorten production time, and a production method thereof.

On the other hand, although erythritol is preferable for use as the base of the sugar coating layer due to its strong sweet taste and low calorie level, it is difficult to form a sugar coating layer and it is easily crystallized. An example of a method for forming a sugar coating layer using erythritol is disclosed in Japanese Patent No. 4391732 that discloses a sugar-coated tablet, obtained by forming a sugar coating layer using a sugar coating liquid that inhibits crystallization of erythritol by combining the erythritol with a polyvinyl alcohol-based resin at a prescribed ratio, and a production method thereof.

In addition, Japanese Patent Application Laid-Open (kokai) No. 2004-137224 discloses that a calorie-free sugar coating layer, which has an extremely smooth texture, exhibits favorable bonding with an uncoated tablet and has adequate strength, can be formed by using a sugar coating liquid containing erythritol, hydroxypropyl methyl cellulose and gum arabic.

In addition, as an example of a method for more easily producing a thin layer sugar-coated tablet, Japanese Patent Application Laid-Open (kokai) No. 2004-155775 discloses a sugar-coated tablet obtained by forming a sugar coating layer with a single sugar coating liquid containing polyethylene glycol, pullulan, polyvinyl pyrrolidone and/or copolyvidone. Japanese Patent Application Laid-Open (kokai) No, 2004-155775 also discloses that a sugar-coated tablet, which has adequate luster and favorable slippage even in the absence of a polishing layer, can be produced by forming a sugar coating layer equivalent to a sub-coating layer and a coloring layer with this sugar coating liquid.

In addition, Japanese Patent Application Laid-Open (kokai) No. 2009-73814 discloses a coating liquid containing erythritol; at least one of calcium lactate, xylitol, and citric acid; at least one of calcium carbonate, and talc; and pullulan for producing a sugar-coated tablet having the advantages of conventional sugar-coated tablets, such as an attractive appearance and superior odor-masking ability, and adequate strength despite having a thin coating layer, a short production time, and is suitable for incorporating components that instable in water, and a thin layer sugar-coated tablet coated with that coating liquid.

In addition, as an example of a method for improving the masking ability of film-coated tablets, Japanese Patent Application Laid-Open (kokai) No. 2008-201711 discloses a coated solid preparation obtained by providing a coating film containing a partially saponified polyvinyl alcohol-based resin on a solid preparation containing L-cysteine or salt thereof.

In addition, Japanese Patent Application Laid-Open (kokai) No. 2008-260778 discloses a film-coated tablet that reduces the odor of an uncoated tablet including a film coating layer which contains a polyvinyl alcohol-based resin and of which the weight is less than 10% by mass relative to the weight of the uncoated tablet, and a method for masking odor that utilizes this film coating layer.

SUMMARY OF THE INVENTION

Problems to be Solved by the Invention

However, a thin layer sugar-coated tablet, which satisfies all of the requirements of odor masking ability, moisture resistance and production ease, has not developed yet.

An object of the present invention is to provide a thin layer sugar-coated preparation, which masks unpleasant odors, has superior moisture resistance and has a simple production procedure, and a production method thereof.

Means for Solving the Problems

As a result of conducting extensive studies in consideration of the aforementioned circumstances, the inventors of the present invention found that a sugar-coated preparation can be produced that has a high ability to mask unpleasant odors and superior moisture resistance by using a sugar coating composition containing at least one type of sugar-alcohol selected from the group consisting of mannitol and erythritol and a polyvinyl alcohol-based resin, even in the case of coating only one layer of a solid composition containing a pharmacologically active ingredient of an uncoated tablet, or the like, thereby leading to completion of the present invention.

Namely, the present invention provides the following (1) to (13).
(1) A production method of a sugar-coated preparation including a solid composition containing a pharmacologically active ingredient and a sugar coating layer,
wherein the production method includes a step of forming the sugar coating layer by a sugar coating composition containing one or more of sugar-alcohols selected from the group consisting of mannitol and erythritol and a polyvinyl alcohol-based resin.
(2) The production method of a sugar-coated preparation according to (1), wherein the sugar coating layer is formed by coating the solid composition containing a pharmacologically active ingredient with the sugar coating composition.
(3) The production method of a sugar-coated preparation according to (1) or (2), wherein the weight ratio between the sugar-alcohol and the polyvinyl alcohol-based resin in the sugar coating composition is 15:2 to 15:20.
(4) The production method of a sugar-coated preparation according to (1) or (2), wherein the weight ratio between the sugar-alcohol and the polyvinyl alcohol-based resin in the sugar coating composition is 15:2.5 to 15:8.
(5) The production method of a sugar-coated preparation according to any one of (1) to (4), wherein the sugar coating layer is formed by coating a single layer, of the sugar coating composition by spraying.
(6) A sugar-coated preparation including a solid composition containing a pharmacologically active ingredient and a sugar coating layer,
wherein the sugar coating layer is made of a sugar coating composition containing one or more of sugar-alcohols selected from the group consisting of mannitol and erythritol and a polyvinyl alcohol-based resin.
(7) The sugar-coated preparation according to (6), wherein the weight ratio between the sugar-alcohol and the polyvinyl alcohol-based resin in the sugar coating composition is 15:2 to 15:20.
(8) The sugar-coated preparation according to (6), wherein the weight ratio between the sugar-alcohol and the polyvinyl alcohol-based resin in the sugar coating composition is 15:2.5 to 15:8.
(9) The sugar-coated preparation according to any one of (6) to (8), wherein the sugar coating layer is formed by coating one layer of the sugar coating composition by spraying.
(10) The sugar-coated preparation according to any one of (6) to (9), wherein the sugar-coated preparation is a tablet, granules or grains.
(11) A sugar coating composition containing one or more of sugar-alcohols selected from the group consisting of mannitol and erythritol, and a polyvinyl alcohol-based resin in an amount more than 0.13 times the amount of the sugar-alcohol in mass ratio.
(12) A sugar-coated preparation coated with the sugar coating composition according to (11).
(13) The sugar-coated preparation according to (12), wherein the sugar-coated preparation is a tablet, granules or grains.

Effects of the Invention

According to the production method of a sugar-coated preparation of the present invention, a sugar-coated preparation can be easily produced in a small number of steps that has a high ability to mask unpleasant odors and has high moisture resistance.

DETAILED DESCRIPTION OF THE INVENTION

Embodiments of the Invention

Figure 1:
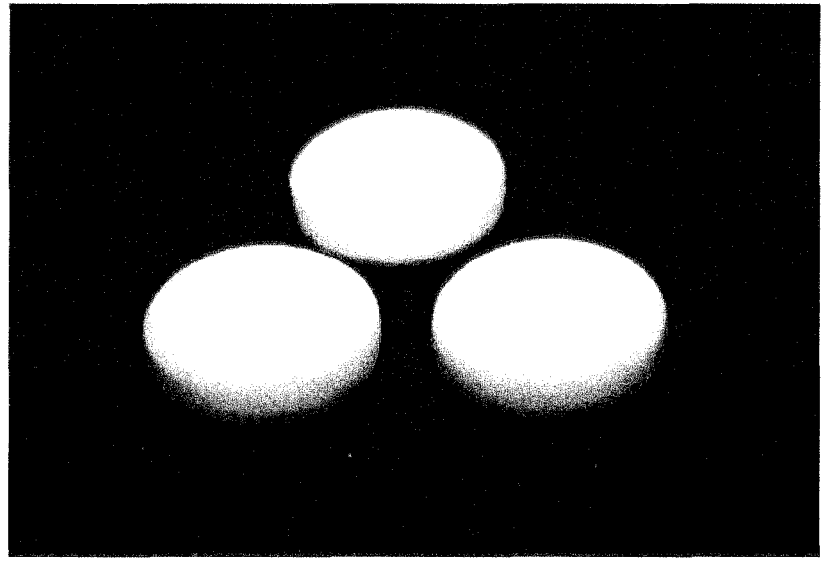
FIG. 1 is a drawing showing the state of a tablet of Example 1 after having been exposed for 48 hours to conditions of 25° C. and 75% RH.

Furthermore, in the present invention and the specification of the present application, a sugar-coated preparation refers to a preparation in which a solid composition containing a pharmacologically active ingredient is coated with a sugar coating layer. Examples of the sugar-coated preparation include sugar-coated tablets in which uncoated tablets are coated with a sugar coating layer, sugar-coated granules in which uncoated granules are coated with a sugar coating layer, and sugar-coated grains in which uncoated grains are coated with a sugar coating layer. In addition, the solid composition containing a pharmacologically active ingredient, such as an uncoated tablet, uncoated granule or uncoated grain, may be collectively referred to as an "uncoated tablet and the like".

<Production Method of Sugar-Coated Preparation>

The production method of a sugar-coated preparation of the present invention (to be referred to as the "production method of the present invention") is a production method of a sugar-coated preparation which includes a solid composition containing a pharmacologically active ingredient and a sugar coating layer, wherein the production method includes a step of forming the sugar coating layer by a sugar coating composition containing one or more of sugar-alcohols selected from the group consisting of mannitol and erythritol and a polyvinyl alcohol-based resin. When the sugar coating composition containing a specific sugar-alcohol and polyvinyl alcohol-based resin is used, it is possible to produce a sugar-coated preparation having a high masking ability even in the case of forming the sugar coating layer with a small coated amount thereof. Moreover, a sugar-coated preparation having superior moisture resistance in addition to superior masking ability can be produced by suitably adjusting the formulation ratio of the specific sugar-alcohol and polyvinyl alcohol-based resin in the sugar coating composition. Accordingly, use of the production method of the present invention makes it possible to easily produce a sugar-coated preparation for which unpleasant odors are masked and degeneration or deterioration of the contents thereof due to moisture absorption is prevented.

The sugar coating composition used in the production method of the present invention contains one or more of sugar-alcohols selected from the group consisting of mannitol and erythritol (to also be described as "sugar-alcohol (Man/ERT)") and a polyvinyl alcohol-based resin. The sugar coating composition may contain mannitol and a polyvinyl alcohol-based resin, may contain erythritol and a polyvinyl alcohol-based resin, or may contain mannitol, erythritol and a polyvinyl alcohol-based resin. Furthermore, in the subsequent descriptions, the "content of the sugar alcohol (Man/ERT)" refers to the total of the content of mannitol and the content of erythritol.

Examples of the polyvinyl alcohol-based resin used in the present invention include partially saponified polyvinyl alcohols (degree of saponification: less than 97 mol %), completely saponified polyvinyl alcohols (degree of saponification: 97 mol % or more), polyvinyl alcohol-polyethylene glycol graft copolymers and polyvinyl alcohol-acrylic acid-methyl methacrylate copolymers. Although any of these may be used in the present invention, partially saponified polyvinyl alcohols are preferable. Although there are no particular limitations thereon, the degree of saponification of the polyvinyl alcohol used in the present invention is preferably 78 mol % to 96 mol %.

There are no particular limitations on the content ratio between the one or more of sugar-alcohols selected from the group consisting of mannitol and erythritol (to also be described as "sugar-alcohol (Man/ERT)") and the polyvinyl alcohol-based resin in the sugar coating composition used in the production method of the present invention. However, in order to be able to demonstrate high masking ability, the polyvinyl alcohol-based resin is preferably contained in the sugar coating composition in an amount more than 0.13 times the amount of the sugar-alcohol (Man/ERT) (mass ratio). In particular, in order to be able to improve moisture resistance in addition to demonstrating high masking ability, the mass ratio between the sugar-alcohol (Man/ERT) and the polyvinyl alcohol-based resin is preferably 15:2 to 15:20, more preferably 15:2 to 15:15, even more preferably 15:2 to 15:8, still more preferably 15:2.5 to 15:8, particularly preferably 15:4 to 15:8, and most preferably 15:4 to 15:6.

The content of the sugar alcohol (Man/ERT) in the sugar coating composition used in the production method of the present invention is preferably 5% by mass to 90% by mass, more preferably 20% by mass to 90% by mass, even more preferably 40% by mass to 86% by mass and still more preferably 65% by mass to 86% by mass as the solid content in the sugar coating composition.

The content of the polyvinyl alcohol-based resin in the sugar coating composition used in the production method of the present invention is preferably 1% by mass to 60% by mass, more preferably 5% by mass to 60% by mass, even more preferably 5% by mass to 40% by mass, still more preferably 8% by mass to 35% by mass, and particularly preferably 14% by mass to 35% by mass as the solid content in the sugar coating composition.

In addition to mannitol or erythritol and the polyvinyl alcohol-based resin, the sugar coating composition used in the production method of the present invention can suitably contain various types of commonly used additives within a range that does not impair the deodorizing property after coating with a small coated amount thereof (masking ability). Examples of such additives include binders, vehicles, fragrances, flavorings, colorants, sweeteners and sour agents.

Examples of binders include powdered gum arabic, alginic acid, sodium alginate, alpha starch, ethyl cellulose, carboxyvinyl polymer, carboxymethyl ethyl cellulose, sodium carboxymethyl starch, carboxymethyl cellulose, sodium carboxymethyl cellulose, xanthan gum, glycerin, crystalline cellulose, crystalline cellulose-carmellose sodium, gelatin, lowly substituted hydroxypropyl cellulose, dextrin, cornstarch, tragacanth, powdered tragacanth, lactose, hydroxyethyl cellulose, hydroxyethyl methyl cellulose, hydroxypropyl cellulose, hydroxypropyl methyl cellulose 2208, hydroxypropyl methyl cellulose 2906, hydroxypropyl methyl cellulose 2910, hydroxypropyl starch, partial alpha starch, pullulan, powdered cellulose, polyethylene glycol, polyvinyl pyrrolidone, macrogol 200, macrogol 300, macrogol 400, macrogol 600, macrogol 1000, macrogol 1500, macrogol 1540, macrogol 4000, macrogol 6000, macrogol 20000, macrogol 35000, methyl cellulose, hydroxypropyl starch, polyoxyethylene[105], and polyoxypropylene[5]glycol.

Examples of vehicles include kaolin, hydrated silicon dioxide, dried aluminum hydroxide, carmellose, carmellose calcium, light silicic anhydride, synthetic aluminum silicate, synthetic hydrotalcite, magnesium oxide, titanium oxide, magnesium stearate, calcium stearate, talc, magnesium carbonate, precipitated calcium carbonate, silicon dioxide, calcium lactate, calcium sulfate, calcium monohydrogen phosphate, calcium hydrogen phosphate, sodium hydrogen phosphate, dipotassium phosphate, potassium dihydrogen phosphate, calcium dihydrogen phosphate and sodium dihydrogen phosphate.

Examples of fragrances and flavorings include natural animal fragrances such as musk, civet, castoreum and ambergris; plant fragrances such as fennel essential oil, orange essential oil, cardamon essential oil, cumin essential oil, cinnamon essential oil, coriander essential oil, jasmine essential oil, spearmint essential oil, geranium essential oil, clove essential oil, vanilla essential oil, mint essential oil, cypress essential oil, sandalwood essential oil, bergamot essential oil, lime essential oil, lavender essential oil, lemon essential oil, lemongrass essential oil, rose essential oil, and rosemary essential oil; and synthetic fragrances such as menthol.

Examples of colorants include natural food dyes such as red rice dye, turmeric dye, caramel, gardenia dye, chlorophyll dye, cochineal dye, safflower dye, marigold dye, purple sweet potato dye and rutin; synthetic food dyes such as red dyes No. 2, 3, 40, 102, 104 and 106, yellow dyes No. 4 and 5, or blue dyes No. 1 and 2; and, yellow iron sesquioxide, iron sesquioxide and titanium oxide.

Examples of sweeteners specifically include aspartame, acesulfame K, dipotassium glycyrrhizate, saccharin, saccharose, stevia and thaumatin.

In addition, examples of sour agents specifically include ascorbic acid, citric acid, tartaric acid and malic acid.

There are no particular limitations on the uncoated tablet and the like that is coated in the production method of a sugarcoated preparation of the present invention provided it is formulated into a preparation. However, since the sugar coating layer which is made of the sugar coating composition has a superior masking ability, a solid composition preferably contains contents that have an unpleasant odor. Examples of contents having an unpleasant odor include vitamin B1 (such as thiamine hydrochloride, thiamine nitrate or fursultiamine hydrochloride), compounds that generate hydrogen sulfide due to deterioration or decomposition and the like (such as L-cysteine), and substances that can be used for pharmaceutical applications by using directly or processing a or a portion of materials present in nature (such as Mallotus Bark, Gambir, Aloe, Epimedium Herb, Ginkgo, Fennel, Mume Fructus, Lindera Root, Bearberry Leaf, Tumeric, Rose Fruit, Siberian Ginseng, Corydalis Tuber, Isodon Japonicus, Astragalus Root, Scutellaria Root, Polygonatum Rhizome, Phellodendron Bark, Prunus Jamasakura Bark, Coptis Rhizome, Polygala Root, Polygonuin Root, Zedoary, Phocae Thstis et Penis, Seahorse, Pueraria Root, Japanese Valerian, Chamomile, Guarana, Glycyrrhiza, Platycodon Root, Chrysanthemum Flower, Immature Orange, Apricot Kernel, Lycium Fruit, Schizonepeta Spike, Cinnamon Bark, Cassia Seed, Gentian, Geranium Herb, Safflower, Red Ginseng, Magnolia Bark, Oriental Bezoar, Acanthopanax Root Bark, Achyranthes Root, Evodia Fruit, Schisandra Fruit, Bupleurum Root, Asiasarum Root, Thyme, Salacia, Salvia, Smilax Rhizome, Hawthorn, Gardenia Fruit, Cornus Fruit, Zanthoxylum Fruit, Jujube Seed, Dioscorea Rhizome, Rehmannia Root, Civet, Peony Root, Cnidium Monnieri Fruit, Plantago Herb, Houttuynia Herb, Amomum Seed, Ginger, Cardamom, Ligustri Fructus, Lumbricus, Magnolia Flower, Senega, Cnidium Rhizoma, Peucedanum Root, Swertia Herb, Atractylodes Lancea Rhizome, Mulberry Bark, Perilla Herb, Rhubarb, Jujube, Clove, Uncaria Hook, Citrus Unshiu Peel, Capsicum, Japanese Angelica Root, *Codonopsis pilosula, Cordyceps sinensis*, Peach Kernel, Bitter Orange Peel, Ipecac, Cuscuta Seed, Eucommia Bark, Nandina Fruit, Corn Silk, Cistanchis Herb, Ginseng, Japanese Honeysuckle, Garlic, Ophiopogon Tuber, Glehnia Root, Pinellia Tuber, Agkistrodon Japonicae, Atractylodes Rhizome, Poria Sclerotium, Blueberry, Sinomenium Stem, Psoralea Semen, Moutan Bark, Hop, Ephedra Herb, Silvervine, Muira Puama, Saussurea Root, Coix Seed, Longan Aril, Japanese Gentian, Scopolia Rhizome, Rosemary, and animal liver, heart or placenta).

In addition, since the sugar coating layer formed by the sugar coating composition also has superior moisture resistance, the solid composition may contain contents susceptible to decomposition by moisture. Examples of the contents susceptible to decomposition by moisture include vitamin A, vitamin B (such as dicethiamine hydrochloride, thiamine hydrochloride, pyridoxine hydrochloride, octotiamine, hydroxocobalamin acetate, cyanocobalamin, thiamine nitrate, bisthiamine nitrate, mecobalamin, thiamine disulfide, bisibuthiamine, bisbentiamine, fursultiamine, benfotiamine, riboflavin butyrate, riboflavin, riboflavin sodium phosphate and pyridoxal phosphate), vitamin C (such as ascorbic acid, calcium ascorbate and sodium ascorbate), vitamin D, vitamin E (such as d-α-tocopherol succinate, dl-α-tocopherol succinate, calcium d-α-tocopherol succinate, dl-α-tocopherol acetate and d-α-tocopherol acetate), vitamin K, vitamin P, as well as aspirin, potassium aspartate, magnesium aspartate, acetaminophen, isopropyl antipyrine, ibuprofen, indometacin, ursodeoxycholic acid, ethenzamide, lysozyme chloride, L-cysteine, diphenhydramine hydrochloride, cloperastine hydrochloride, phenylpropanolamine hydrochloride, noscapine hydrochloride, dl-methylephedrine hydrochloride, orotic acid, gamma-oryzanol, guaifenesin, glucuronolactone, glucuronic acid amide, ketoprofen, L-cysteine, cimetidine, dextromethorphan hydrobromide, nicotinamide, nicotinic acid, noscapine, calcium pantothenate, calcium pantothenate type S, sodium pantothenate, biotin, famotidine, clemastine fumarate, d-chlorpheniramine maleate, dl-chlorpheniramine maleate, mequitazine, folic acid, dihydrocodeine phosphate and codeine phosphate.

The production method of the present invention is characterized in that the sugar coating layer is formed by the aforementioned sugar coating composition. For example, the sugar coating layer can be formed by directly coating an uncoated tablet and the like with the sugar coating composition. Although there are no particular limitations on the coated amount of the sugar coating composition, it is preferably less than the amount of the uncoated tablet and the like, more preferably 60% by mass or less of the uncoated tablet and the like, and more preferably 10% by mass to 50% by mass of the uncoated tablet and the like.

There are no particular limitations on the method used to coat with the sugar coating composition, and a method can be suitably selected and used from among methods used when coating a solid substance with a liquid composition. For example, a dropping method or spraying method may be used, a sugar coating pan may be used, or the sugar coating composition may be manually applied to uncoated tablets. In the present invention, a spraying method is used preferably since this enables a thin sugar coating layer to be formed on, the surface of uncoated tablets using a small coated amount thereof.

The sugar-coated preparation produced in the production method of the present invention preferably includes an uncoated tablet and the like and a sugar coating layer formed from the sugar coating composition that coats the uncoated tablet. As a result of the coating of the uncoated tablet and the like with only a single layer made of the sugar coating composition, the coating process can be simplified and a sugar-coated preparation can be produced more easily and at lower cost.

Since the sugar coating composition used in the production method of the present invention demonstrates an extremely high masking ability, a sugar-coated preparation that masks the odor of the uncoated tablet and the like can be produced without having a protective coating layer in the manner of conventional thin layer sugar-coated tablets. In addition, the surface of the sugar coating layer formed by the sugar coating composition has few surface irregularities, has adequate luster and has favorable slippage. Consequently, a sugar-coated preparation having a favorable appearance can be obtained without additionally forming a polishing layer on the surface of the sugar coating layer. In other words, use of the sugar coating composition makes it possible to produce a sugar-coated preparation having a high masking ability and favorable appearance by forming only a single layer of the sugar coating layer without having form multiple layers.

Furthermore, in the production method of the present invention, instead of an uncoated tablet and the like, a film-coated tablet, obtained by coating an uncoated tablet and the like with a protective coating layer, may be coated with the sugar coating composition to form a sugar coating layer. In this case as well, a step for forming a polishing layer and so forth used in the production process of sugar-coated preparations, such as conventional thin layer sugar-coated tablets, can be omitted.

In addition, the production method of the present invention may be any methods which form the sugar-coated layer using the sugar coating composition. The obtained sugar-coated preparation may be a multi-coated preparation having any sugar coating layer in addition to the sugar coating layer made of the sugar coating composition. For example, after having coated an uncoated tablet with a protective coating layer, a tablet obtained by coating with a sub-coating layer made of a sugar coating composition other than the aforementioned sugar coating composition may be coated with the sugar coating composition to form a sugar coating layer.

The sugar-coated preparation produced according to the production method of the present invention (sugar-coated preparation of the present invention) can be used in various applications such as pharmaceuticals, quasi drugs, cosmetics, functional foods, health foods or ordinary foods in the same manner as sugar-coated preparations produced according to other production methods.

In addition, the sugar coating composition used in the production method of the present invention can also be used to form sugar coatings of granules or grains in addition to tablets in the same manner as other sugar coating compositions.

EXAMPLES

Although the following provides a more detailed explanation of the present invention by indicating examples thereof, the present invention is not limited to the following examples.

Example 1

120 g of L-cysteine (Taenaka Kogyo Co., Ltd.), 300 g of crystalline cellulose (Ceolus PH-101, Asahi Kasei Chemicals Corp.), 132 g of potato starch (Nippon Starch Chemical Co., Ltd.) were subjected to a fluidized bed granulation method to produce granules using a fluidized bed granulator (MP-01, Powrex Corp.) by spraying 180 g of an aqueous solution of 10% hydroxypropyl cellulose (HPC-SL, Nippon Soda Co., Ltd.). Subsequently, the obtained granules were sized using a sieve (30 mesh) to obtain a sized powder. 2.82 g of silicon dioxide (Maikon F, Tomita Pharmaceutical Co., Ltd.) and 2.82 g of magnesium stearate (Taihei Chemical Industrial Co., Ltd.) were mixed with 536 g of the resulting sized powder in a plastic bag, and the resulting mixed powder was tableted with a rotary tableting machine (Hata Iron Works Co., Ltd.) to a weight of 120 mg, diameter of 7 mm and thickness of 3.8 mm per tablet to obtain uncoated tablets. The composition of the uncoated tablets (amounts in 8 uncoated tablets) is shown in Table 1.

TABLE 1

| Component | Incorporated Amount |
| --- | --- |
| L-cysteine | 200 mg |
| Crystalline cellulose (Ceolus PH-101) | 500 mg |
| Potato starch | 220 mg |
| Hydroxypropyl cellulose (HPC-SL) | 30 mg |
| Silicon dioxide | 5 mg |
| Magnesium stearate | 5 mg |
| Total | 960 mg |

A sugar coating liquid obtained by dissolving 120 g of D-mannitol (Mannit P, Towa Chemical. Industry Co., Ltd.) and 32 g of partially saponified polyvinyl alcohol (Gohsenol EG-05, Nippon Synthetic Chemical Industry Co., Ltd.) in 648 g of purified water (ratio between D-mannitol and partially saponified polyvinyl alcohol=15:4), was coated onto 100 g of the resulting uncoated tablets at 50% by mass of the uncoated tablets using a coating machine (Doria Coater DRC-200, Powrex Corp.) to obtain thin layer sugar-coated tablets.

Comparative Example 1

Thin layer sugar-coated tablets were obtained in the same manner as Example 1 with the exception of using a sugar coating liquid obtained by dissolving and suspending 50 g of erythritol (Nikken Chemical Laboratory Co., Ltd.), 28 g of talc (Shokozan Mining Co., Ltd.), 10 g of crystalline cellulose (Ceolus PH-F20JP) and 12 g of powdered gum arabic (San-Ei Yakuhin Boeki Co., Ltd.) in 120 g of purified water.

Example 2

312.5 g of L-cysteine (Taenaka Kogyo Co., Ltd.), 781.25 g of crystalline cellulose (Ceolus PH-101, Asahi Kasei Chemicals Corp.), 343.75 g of potato starch (Nippon Starch Chemical Co., Ltd.) were subjected to a fluidized bed granulation method to produce granules using a fluidized bed granulator (FLO-25, Freund Corp.) by spraying 468.8 g of an aqueous solution of 10% hydroxypropyl cellulose (HPC-SL, Nippon Soda Co., Ltd.). (The uncoated tablet composition was the same as in Table 1 of Example 1.) Subsequently, the granules were sized using a sieve (30 mesh) to obtain a sized powder. 6.79 g of silicon dioxide (Maikon F, Tomita Pharmaceutical Co., Ltd.) and 6.79 g of magnesium stearate (Taihei Chemical Industrial Co., Ltd.) were mixed with 1291 g of the resulting sized powder in a plastic bag, and the resulting mixed powder was tableted with a rotary tableting machine (Hata Iron Works Co., Ltd.) to a weight of 120 mg, diameter of 7 mm and thickness of 3.8 mm per tablet to obtain uncoated tablets.

A sugar coating liquid obtained by dissolving 120 g of D-mannitol (Mannit P, Towa Chemical Industry Co., Ltd.) and 20 g of partially saponified polyvinyl alcohol (Gohsenol EG-05, Nippon Synthetic Chemical Industry Co., Ltd.) in 560 g of purified water (ratio between D-mannitol and partially saponified polyvinyl alcohol=15:2.5), was coated onto 200 g of the resulting uncoated tablets at 50% by mass of the uncoated tablets using a coating machine (Doria Coater DRC-200, Powrex Corp.) to obtain sugar-coated tablets.

Example 3

Thin layer sugar-coated tablets were obtained in the same manner as Example 2 with the exception of using a sugar coating liquid obtained by dissolving 240 g of D-mannitol (Mannit P, Towa Chemical Industry Co., Ltd.) and 64 g of partially saponified polyvinyl alcohol (Gohsenol EG-05, Nippon Synthetic Chemical Industry Co., Ltd.) in 1216 g of purified water (ratio between D-mannitol and partially saponified polyvinyl alcohol=15:4).

Example 4

Thin layer sugar-coated tablets were obtained in the same manner as Example 2 with the exception of using a sugar coating liquid, obtained by dissolving 120 g of D-mannitol (Mannit P, Towa Chemical Industry Co., Ltd.) and 48 g of partially saponified polyvinyl alcohol (Gohsenol EG-05, Nippon Synthetic Chemical Industry Co., Ltd.) in 672 g of purified water (ratio between D-mannitol and partially saponified polyvinyl alcohol=15:6).

Example 5

Thin layer sugar-coated tablets were obtained in the same manner as Example 2 with the exception of using a sugar coating liquid obtained by dissolving 120 g of D-mannitol (Mannit P, Towa Chemical Industry Co., Ltd.) and 64 g of partially saponified polyvinyl alcohol (Gohsenol EG-05, Nippon Synthetic Chemical Industry Co., Ltd.) in 736 g of purified water (ratio between D-mannitol and partially saponified polyvinyl alcohol=15:8).

Example 6

Thin layer sugar-coated tablets were obtained in the same manner as Example 2 with the exception of using a sugar coating liquid obtained by dissolving 120 g of erythritol (Nikken Chemical Laboratory Co., Ltd.) and 20 g of partially saponified polyvinyl alcohol (Gohsenol EG-05, Nippon Synthetic Chemical Industry Co., Ltd.) in 560 g of purified water (ratio between erythritol and partially saponified polyvinyl alcohol=15:2.5).

Example 7

Thin layer sugar-coated tablets were obtained in the same manner as Example 2 with the exception of using a sugar coating liquid obtained by dissolving 120 g of erythritol (Nikken Chemical Laboratory Co., Ltd.) and 32 g of partially saponified polyvinyl alcohol (Gohsenol EG-05, Nippon Synthetic Chemical Industry Co., Ltd.) in 608 g of purified water (ratio between erythritol and partially saponified polyvinyl alcohol=15:4).

Example 8

Thin layer sugar-coated tablets were obtained in the same manner as Example 2 with the exception of using a sugar coating liquid obtained by dissolving 120 g of erythritol (Nikken Chemical Laboratory Co., Ltd.) and 48 g of partially saponified polyvinyl alcohol (Gohsenol EG-05, Nippon Synthetic Chemical Industry Co., Ltd.) in 672 g of purified water (ratio between erythritol and partially saponified polyvinyl alcohol=15:6).

Example 9

Thin layer sugar-coated tablets were obtained in the same manner as Example 2 with the exception of using a sugar coating liquid obtained by dissolving 120 g of erythritol (Nikken Chemical Laboratory Co., Ltd.) and 64 g of partially saponified polyvinyl alcohol (Gohsenol EG-05, Nippon Synthetic Chemical Industry Co., Ltd.) in 736 g of purified water (ratio between erythritol and partially saponified polyvinyl alcohol=15:8).

Example 10

Thin, layer sugar-coated tablets were obtained in the same manner as Example 2 with the exception of using a sugar coating liquid obtained by dissolving 120 g of D-mannitol (Mannit P, Towa Chemical Industry Co., Ltd.) and 16 g of partially saponified polyvinyl alcohol (Gohsenol EG-05, Nippon Synthetic Chemical Industry Co., Ltd.) in 544 g of purified water (ratio between D-mannitol and partially saponified polyvinyl alcohol=15:2).

Example 11

Thin layer sugar-coated tablets were obtained in, the same manner as Example 2 with the exception of using a sugar coating liquid obtained by dissolving 120 g of D-mannitol (Mannit P, Towa Chemical Industry Co., Ltd.) and 96 g of partially saponified polyvinyl alcohol (Gohsenol EG-05, Nippon Synthetic Chemical Industry Co., Ltd.) in 864 g of purified water (ratio between D-mannitol and partially saponified polyvinyl alcohol=15:12).

Example 12

Thin layer sugar-coated tablets were obtained in the same manner as Example 2 with the exception of using a sugar coating liquid obtained by dissolving 120 g of D-mannitol (Mannit P, Towa Chemical Industry Co., Ltd.) and 120 g of partially saponified polyvinyl alcohol (Gohsenol EG-05, Nippon Synthetic Chemical Industry Co., Ltd.) in 960 g of purified water (ratio between D-mannitol and partially saponified polyvinyl alcohol=15:15).

Example 13

Thin layer sugar-coated tablets were obtained in the same manner as Example 2 with the exception of using a sugar coating liquid obtained by dissolving 120 g of D-mannitol (Mannit P, Towa Chemical Industry Co., Ltd.) and 160 g of partially saponified polyvinyl alcohol (Gohsenol EG-05, Nippon Synthetic Chemical Industry Co., Ltd.) in 2520 g of purified water (ratio between D-mannitol and partially saponified polyvinyl alcohol=15:20).

Example 14

Thin layer sugar-coated tablets were obtained in the same manner as Example 2 with the exception of using a sugar coating liquid obtained by dissolving 120 g of erythritol (Nikken Chemical Laboratory Co., Ltd.) and 16 g of partially saponified polyvinyl alcohol (Gohsenol EG-05, Nippon Synthetic Chemical Industry Co., Ltd.) in 544 g of purified water (ratio between erythritol and partially saponified polyvinyl alcohol=15:2).

Example 15

Thin layer sugar-coated tablets were obtained in the same manner as Example 2 with the exception of using a sugar coating liquid obtained by dissolving 120 g of erythritol (Nikken Chemical Laboratory Co., Ltd.) and 96 g of partially saponified polyvinyl alcohol (Gohsenol EG-05, Nippon Synthetic Chemical Industry Co., Ltd.) in 864 g of purified water (ratio between erythritol and partially saponified polyvinyl alcohol=15:12).

Example 16

Thin layer sugar-coated tablets were obtained in the same manner as Example 2 with the exception of using a sugar coating liquid obtained by dissolving 120 g of erythritol (Nikken Chemical Laboratory Co., Ltd.) and 120 g of partially saponified polyvinyl alcohol (Gohsenol EG-05, Nippon Synthetic Chemical Industry Co., Ltd.) in 960 g of purified water (ratio between erythritol and partially saponified polyvinyl alcohol 15:15).

Example 17

Thin layer sugar-coated tablets were obtained in the same manner as Example 2 with the exception of using a sugar coating liquid obtained by dissolving 120 g of erythritol (Nikken Chemical Laboratory Co., Ltd.) and 160 g of partially saponified polyvinyl alcohol (Gohsenol EG-05, Nippon Synthetic Chemical Industry Co., Ltd.) in 2520 g of purified water (ratio between erythritol and partially saponified polyvinyl alcohol=15:20).

Comparative Example 2

Film-coated tablets were obtained by coating a 15% aqueous solution of a polyvinyl alcohol-containing film coating composition (Opadry AMB, Colorcon Japan LLC) onto 100 g of the uncoated tablets of Example 2 using a coating machine (Doria Coater DRC-200, Powrex Corp.) at 5% by mass of the uncoated tablets.

Comparative Example 3

Thin layer sugar-coated tablets were obtained in the same manner as Example 2 with the exception of using a sugar coating liquid obtained by dissolving 120 g of D-mannitol (Mannit P, Towa Chemical Industry Co., Ltd.) and 8 g of partially saponified polyvinyl alcohol (Gohsenol EG-05, Nippon Synthetic Chemical Industry Co., Ltd.) in 512 g of purified water (ratio between D-mannitol and partially saponified polyvinyl alcohol 15:1).

Comparative Example 4

Although coating was carried out in the same manner as Example 2 with the exception of using a sugar coating liquid obtained by dissolving 120 g of D-mannitol (Mannit P, Towa Chemical Industry Co., Ltd.) and 200 g of partially saponified polyvinyl alcohol (Gohsenol EG-05, Nippon Synthetic Chemical Industry Co., Ltd.) in 2880 g of purified water (ratio between D-mannitol and partially saponified polyvinyl alcohol=15:25), a coating was unable to be formed and thin layer sugar-coated tablets were unable to be obtained.

Comparative Example 5

Thin layer sugar-coated tablets were obtained in the same manner as Example 2 with the exception of using a sugar coating liquid obtained by dissolving 120 g of erythritol (Nikken Chemical Laboratory Co., Ltd.) and 8 g of partially saponified polyvinyl alcohol (Gohsenol EG-05, Nippon Synthetic Chemical Industry Co., Ltd.) in 512 g of purified water (ratio between erythritol and partially saponified polyvinyl alcohol=15:1).

Comparative Example 6

Although coating was carried out in the same manner as Example 2 with the exception of using a sugar coating liquid obtained by dissolving 120 g of erythritol (Nikken Chemical Laboratory Co., Ltd.) and 200 g of partially saponified polyvinyl alcohol (Gohsenol EG-05, Nippon Synthetic Chemical Industry Co., Ltd.) in 2880 g of purified water (ratio between erythritol and partially saponified polyvinyl alcohol=15:25), a coating was unable to be formed and thin layer sugar-coated tablets were unable to be obtained.

[Evaluation of Unpleasant Odor Masking: Comparison with Existing Technology]

After placing 50 tablets each of the thin layer sugar-coated tablets of Example 1 and Comparative Example 1 in standard bottles (6K), the bottles were placed and sealed in aluminum pouches with the bottles left open. Subsequently, the aluminum pouches were stored for 1 day at 60° C. and the unpleasant odor of L-cysteine (hydrogen sulfide) generated within the aluminum pouches was measured using a Kitagawa gas detector tube (Komyo Rikagaku Kogyo K.K.) to evaluate odor masking effects.

<Parameter>

Amount of hydrogen sulfide generated (ppm): Concentration of hydrogen sulfide contained in aluminum pouch <Results>

As shown in Table 2, the thin layer sugar-coated tablets having a single layer coating of Comparative Example 1 resulted in generation of an unpleasant odor (hydrogen sulfide) and masking effects were inadequate. In contrast, there was no unpleasant odor whatsoever in the case of the thin layer sugar-coated tablets having a single layer coating of Example 1.

TABLE 2

| Hydrogen sulfide generation (ppm) (60° C., 1 day) | | |
|---|---|---|
| No. | Example 1 | Comparative Example 1 |
| 1 | 0 | 3 |
| 2 | 0 | 3 |
| 3 | 0 | 3 |

[Evaluation of Unpleasant Odor Masking: Study of Weight Ratio]

After placing 50 tablets each of the uncoated tablets of Example 2 and the thin layer sugar-coated tablets of Examples 2 to 17 and Comparative Examples 2, 3 and 5 in standard bottles (6K), the bottles were placed and sealed in aluminum pouches with the bottles left open. Subsequently, the aluminum pouches were stored for 1 day or 1 week at 60° C. and the unpleasant odor of L-cysteine (hydrogen sulfide) generated within the aluminum pouches was measured using a Kitagawa gas detector tube (Komyo Rikagaku Kogyo K.K.) to evaluate odor masking effects.

<Parameter>

Amount of hydrogen sulfide generated (ppm): Concentration of hydrogen sulfide contained in aluminum pouch <Results>

The results for storing the thin layer sugar-coated tablets of Examples 2 to 9 for 1 day at 60° C. are shown in Table 3, and the results for storing the same tablets for 1 week at 60° C. are shown in Table 4. In, addition, the results for storing the thin layer sugar-coated tablets of Comparative Examples 2 and 3 and Examples 10 to 13 for 1 week at 60° C. are shown in Table 5, and the results for storing the thin layer sugar-coated tablets of Comparative Example 5 and Examples 14 to 17 for 1 week at 60° C. are shown in Table 6.

In Tables 2 to 6, the numbers in parentheses shown below the numbers of the examples and comparative examples represent the weight ratio between D-mannitol or erythritol and partially saponified polyvinyl alcohol ([D-mannitol or erythritol content]:[partially saponified polyvinyl alcohol content]) of the sugar coating liquid used. Thin layer sugar-coated tablets coated using a coating liquid in which the weight ratio between D-mannitol or erythritol and partially saponified polyvinyl alcohol was 15:2 to 15:20 (Examples 2 to 17) demonstrated a considerable decrease in unpleasant odor (hydrogen sulfide) in comparison with thin layer sugar-coated tablets coated using a coating liquid in which the weight ratio between D-mannitol or erythritol and partially saponified polyvinyl alcohol was 15:1 (Comparative Examples 2 to 5). In particular, thin layer sugar-coated tablets coated using a coating liquid in which the weight ratio between D-mannitol or erythritol and partially saponified polyvinyl alcohol was 15:2.5 to 15:15 (Examples 2 to 9, 11, 12, 15 and 16) generated no unpleasant odor (hydrogen sulfide) whatsoever or demonstrated a considerable decrease in unpleasant odor (hydrogen sulfide). On the basis of these results, the production method of the present invention clearly enabled the production of thin layer sugar-coated tablets that masked unpleasant odor.

TABLE 3

| | | Hydrogen sulfide generation (ppm) (60° C., 1 day) | | | | | | | |
|---|---|---|---|---|---|---|---|---|---|
| | Uncoated | Examples | | | | | | | |
| No. | tablets of Example 2 | 2 (15:2.5) | 3 (15:4) | 4 (15:6) | 5 (15:8) | 6 (15:2.5) | 7 (15:4) | 8 (15:6) | 9 (15:8) |
| 1 | 5 | 0 | 0 | 0 | 0 | 0 | 0 | 0 | 0 |
| 2 | 5 | 0 | 0 | 0 | 0 | 0 | 0 | 0 | 0 |
| 3 | 5 | 0 | 0 | 0 | 0 | 0 | 0 | 0 | 0 |
| 4 | 5 | 0 | 0 | 0 | 0 | 0 | 0 | 0 | 0 |
| 5 | 5 | 0 | 0 | 0 | 0 | 0 | 0 | 0 | 0 |
| 6 | 5 | 0 | 0 | 0 | 0 | 0 | 0 | 0 | 0 |
| 7 | 6 | 0 | 0 | 0 | 0 | 0 | 0 | 0 | 0 |
| 8 | 7 | 0 | 0 | 0 | 0 | 0 | 0 | 0 | 0 |
| 9 | 6 | 0 | 0 | 0 | 0 | 0 | 0 | 0 | 0 |
| 10 | 5 | 0 | 0 | 0 | 0 | ≤0.2 | 0 | 0 | 0 |

TABLE 4

| | | Hydrogen sulfide generation (ppm) (60° C., 1 week) | | | | | | | |
|---|---|---|---|---|---|---|---|---|---|
| | Uncoated | Examples | | | | | | | |
| No. | tablets of Example 2 | 2 (15:2.5) | 3 (15:4) | 4 (15:6) | 5 (15:8) | 6 (15:2.5) | 7 (15:4) | 8 (15:6) | 9 (15:8) |
| 1 | ≥60 | 0.7 | 0 | 0 | 0 | 0.3 | 0 | 0 | 0 |
| 2 | ≥60 | 0 | 0 | 0 | 0 | 0 | 0 | 0 | 0 |
| 3 | ≥60 | 0 | 0 | 0 | 0 | 0 | 0 | 0 | 0 |
| 4 | ≥60 | 0.8 | 0 | 0 | 0 | 0 | 0 | 0 | 0 |
| 5 | ≥60 | 0 | 0 | 0 | 0 | 0 | 0 | 0 | 0 |
| 6 | 54 | 0 | 0 | 0 | 0 | 0.6 | 0 | 0 | 0 |
| 7 | ≥60 | 0.5 | 0 | 0 | 0 | 0 | 0 | 0 | 0 |
| 8 | ≥60 | 0 | 0 | 0 | 0 | 0.4 | 0 | 0 | 0 |
| 9 | ≥60 | 0.2 | 0 | 0 | 0 | 0 | 0 | 0 | 0 |
| 10 | ≥60 | 1.5 | 0 | 0 | 0 | 0.4 | 0 | 0 | 0 |

TABLE 5

Hydrogen sulfide generation (ppm) (60° C., 1 week)

| No. | Comp. Examples 2 | Comp. Examples 3 (15:1) | Examples 10 (15:2) | Examples 11 (15:12) | Examples 12 (15:15) | Examples 13 (15:20) |
|---|---|---|---|---|---|---|
| 1  | 21 | ≥60 | 7 | 0 | 0 | 0 |
| 2  | 23 | 58  | 6 | 0 | 0 | 0 |
| 3  | 30 | ≥60 | 4 | 0 | 0 | ≤0.2 |
| 4  | 30 | 40  | 5 | 0 | 0 | 0 |
| 5  | 44 | ≥60 | 5 | 0 | 0 | ≤0.2 |
| 6  | 30 | ≥60 | 1 | 0 | 0 | 0.2 |
| 7  | 38 | 44  | 8 | 0 | 0 | 0 |
| 8  | 28 | 42  | 5 | 0 | 0 | 0 |
| 9  | 28 | ≥60 | 5 | 0 | 0 | 0 |
| 10 | 60 | ≥60 | 2 | 0 | 0 | ≤0.2 |

TABLE 6

Hydrogen sulfide generation (ppm) (60° C., 1 week)

| No. | Comp. Example 5 (15:1) | Examples 14 (15:2) | Examples 15 (15:12) | Examples 16 (15:15) | Examples 17 (15:20) |
|---|---|---|---|---|---|
| 1  | 40  | 2   | 0 | 0 | 0 |
| 2  | ≥60 | 4   | 0 | 0 | 0 |
| 3  | ≥60 | 0   | 0 | 0 | 0 |
| 4  | ≥60 | 2   | 0 | 0 | 0 |
| 5  | ≥60 | 1   | 0 | 0 | 0 |
| 6  | ≥60 | 3   | 0 | 0 | 0 |
| 7  | ≥60 | 1   | 0 | 0 | 0 |
| 8  | ≥60 | 2.5 | 0 | 0 | 0 |
| 9  | ≥60 | 3   | 0 | 0 | 0 |
| 10 | ≥60 | 3   | 0 | 0 | 0 |

[Evaluation of Moisture Resistance: Comparison with Existing Technology]

25 tablets each of the thin layer sugar-coated tablets of Example 1 and Comparative Example 1 were exposed to conditions of 25° C. and 75% RH followed by evaluating moisture resistance according to change in weight 48 hours later.

<Parameter>

Moisture uptake(%)=$(B-A)/A \times 100$

Moisture uptake (%): Amount of moisture absorbed by 25 tablets
A: Weight of 25 tablets before moisture absorption
B: Weight of 25 tablets after moisture absorption <Results>

Figure 2:
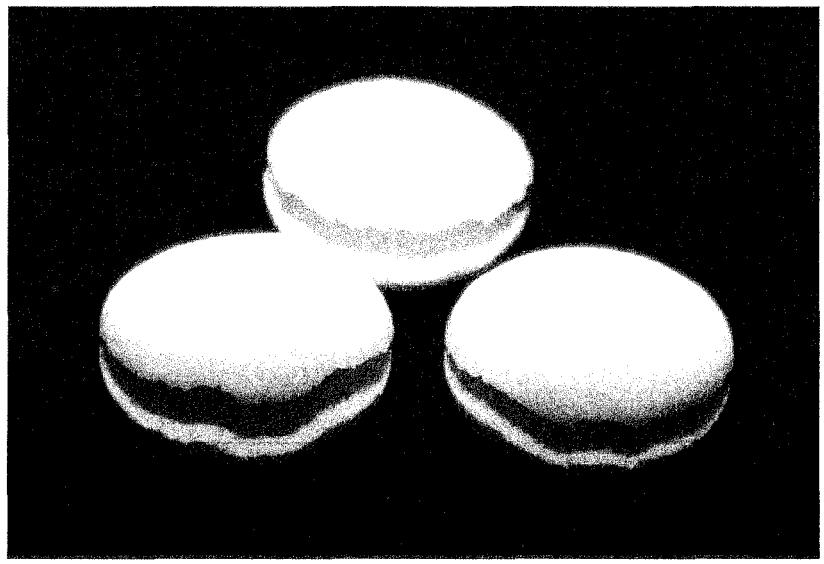
FIG. 2 is a drawing showing the state of a tablet of Comparative Example 1 after having been exposed for 48 hours to conditions of 25° C. and 75% RH.

As shown in Table 7 and FIGS. 1 and 2, in contrast to the thin layer sugar-coated tablets of Comparative Example 1 cracking due to absorption of moisture and demonstrating a high degree of moisture absorption, moisture absorption of the sugar-coated tablets of Example 1 was low, and cracking and other changes in appearance were not observed. On the basis of these results, the production method of the present invention clearly enables the production of thin layer sugar-coated tablets having high moisture resistance.

TABLE 7

Moisture Uptake (%)

| Comparative Example 1 | Example 1 |
|---|---|
| 5.59 | 0.32 |

[Evaluation of Moisture Resistance: Study of Weight Ratio]

25 tablets each of the uncoated tablets of Example 2 and the thin layer sugar-coated tablets of Examples 2 to 17 and Comparative Examples 2, 3 and 5 were exposed to conditions of 25° C. and 75% RH followed by evaluating moisture resistance according to change in weight 48 hours later.

<Parameter>

Moisture uptake(%)=$(B-A)/A \times 100$

Moisture uptake (%): Amount of moisture absorbed by 25 tablets
A: Weight of 25 tablets before moisture absorption
B: Weight of 25 tablets after moisture absorption <Results>

The results of measuring moisture uptake for the thin layer sugar-coated tablets of Examples 2 to 9 are shown in Table 8, the results of measuring moisture uptake for the thin layer sugar-coated tablets of Comparative Examples 2 and 3 and Examples 10 to 13 are shown in Table 9, and the results of measuring moisture uptake for the thin layer sugar-coated tablets of Comparative Example 5 and Examples 14 to 17 are shown in Table 10.

In Tables 8 to 10, the numbers in parentheses shown below the numbers of the examples and comparative examples represent the weight ratio between D-mannitol or erythritol and partially saponified polyvinyl alcohol ([D-mannitol or erythritol content]:[partially saponified polyvinyl alcohol content]) of the sugar coating liquid used. As a result, thin layer sugar-coated tablets coated with a coating liquid in which the weight ratio between D-mannitol or erythritol and partially saponified polyvinyl alcohol was 15:2 to 15:20 (Examples 2 to 17) all demonstrated moisture uptakes of 2% or less and had extremely low moisture absorption. In particular, as shown in Table 8, thin layer sugar-coated tablets coated with a coating liquid in which the weight ratio between D-mannitol or erythritol and partially saponified polyvinyl alcohol was 15:2.5 to 15:8 (Examples 2 to 9) demonstrated considerably decreased moisture absorption in comparison with the uncoated tablets of Example 2. On the basis of these results, the production method of the present invention clearly enables the production of thin layer sugar-coated tablets having high moisture resistance.

TABLE 8

Moisture Uptake (%)

| No. | Uncoated tablets of Example 2 | Examples 2 (15:2.5) | 3 (15:4) | 4 (15:6) | 5 (15:8) | 6 (15:2.5) | 7 (15:4) | 8 (15:6) | 9 (15:8) |
|---|---|---|---|---|---|---|---|---|---|
| 1 | 6.69 | 0.24 | 0.23 | 0.36 | 0.58 | 0.20 | 0.36 | 0.61 | 0.94 |
| 2 | 6.70 | 0.29 | 0.27 | 0.40 | 0.62 | 0.24 | 0.40 | 0.65 | 0.96 |
| 3 | 6.70 | 0.26 | 0.24 | 0.38 | 0.61 | 0.22 | 0.37 | 0.62 | 0.96 |

TABLE 9

| | Moisture Uptake (%) | | | | |
|---|---|---|---|---|---|
| | Comparative Examples | Examples | | | |
| No. | 2 | 3 (15:1) | 10 (15:2) | 11 (15:12) | 12 (15:15) | 13 (15:20) |
| 1 | 5.94 | 3.47 | 0.36 | 1.01 | 1.11 | 0.99 |
| 2 | 5.94 | 3.50 | 0.36 | 1.02 | 1.14 | 1.01 |
| 3 | 5.98 | 3.23 | 0.36 | 1.02 | 1.15 | 1.00 |

TABLE 10

| | Moisture Uptake (%) | | | | |
|---|---|---|---|---|---|
| | Comparative Example | Examples | | | |
| No. | 5 (15:1) | 14 (15:2) | 15 (15:12) | 16 (15:15) | 17 (15:20) |
| 1 | 0.16 | 0.18 | 1.54 | 1.96 | 1.66 |
| 2 | 0.19 | 0.18 | 1.58 | 1.94 | 1.75 |
| 3 | 0.15 | 0.19 | 1.55 | 1.91 | 1.74 |

Comparative Example 7

Thin layer sugar-coated tablets were obtained in the same manner as Example 2 with the exception of using a sugar coating liquid obtained by dissolving 120 g of xylitol (Towa Chemical Industry Co., Ltd.) and 48 g of partially saponified polyvinyl alcohol (Gohsenol EG-05, Nippon Synthetic Chemical Industry Co., Ltd.) in 672 g of purified water (ratio between xylitol and partially saponified polyvinyl alcohol=15:6).

Comparative Example 8

Although coating was carried out in the same manner as Example 2 with the exception of using a sugar coating liquid obtained by dissolving 120 g of maltitol (Towa Chemical Industry Co., Ltd.) and 32 g of partially saponified polyvinyl alcohol (Gohsenol EG-05, Nippon Synthetic Chemical Industry Co., Ltd.) in 608 g of purified water (ratio between maltitol and partially saponified polyvinyl alcohol=15:4), a coating was unable to be formed and thin layer sugar-coated tablets were unable to be obtained.

Comparative Example 9

Although coating was carried out in the same manner as Example 2 with the exception of using a sugar coating liquid obtained by dissolving 120 g of maltitol (Towa Chemical Industry Co., Ltd.) and 120 g of partially saponified polyvinyl alcohol (Gohsenol EG-05, Nippon Synthetic Chemical Industry Co., Ltd.) in 960 g of purified water (ratio between maltitol and partially saponified polyvinyl alcohol=15:15), a coating was unable to be formed and thin layer sugar-coated tablets were unable to be obtained.

[Evaluation of Unpleasant Odor Masking: Case of Using Xylitol]

The thin layer sugar-coated tablets of Comparative Example 7 were stored for 1 week at 60° C. followed by measurement of the amount of hydrogen sulfide generated in the same manner as Example 2 to evaluate odor masking effects.

The results of measuring hydrogen sulfide generation are shown in Table 11. The thin layer sugar-coated tablets of Comparative Example 7, in which the weight ratio between xylitol and partially saponified polyvalent alcohol in the coating liquid was 15:6, demonstrated an amount of hydrogen sulfide generated of 10 ppm or more and odor masking effects were not observed.

TABLE 11

| Hydrogen Sulfide Generation (ppm) | |
|---|---|
| No. | Comparative Example 7 |
| 1 | 21 |
| 2 | 20 |
| 3 | 14 |
| 4 | 10 |
| 5 | 16 |
| 6 | 14 |
| 7 | 13 |
| 8 | 21 |
| 9 | 13 |
| 10 | 15 |

[Evaluation of Moisture Resistance: Case of Using Xylitol]

25 tablets each of the thin layer sugar-coated tablets of Comparative Example 7 were exposed to 25° C. and 75% RH in the same manner as Example 2 followed by followed by evaluating moisture resistance according to change in weight 48 hours later.

The results of measuring moisture uptake are shown in Table 12. The thin layer sugar-coated tablets of Comparative Example 7, in which the weight ratio between xylitol and partially saponified polyvalent alcohol in the coating liquid was 15:6, demonstrated moisture uptake of 3% or more and had inferior moisture resistance.

TABLE 12

| Moisture Uptake (%) | |
|---|---|
| No. | Comparative Example 7 |
| 1 | 3.74 |
| 2 | 3.29 |
| 3 | 3.60 |

Example 18

Thin layer sugar-coated tablets were obtained in the same manner as Example 2 with the exception of using a sugar coating liquid obtained by dissolving 120 g of D-mannitol (Mannit P, Towa Chemical Industry Co., Ltd.) and 32 g of completely saponified polyvinyl alcohol (Kyowa Pure Chemical Co., Ltd.) in 608 g of purified water (ratio between D-mannitol and completely saponified polyvinyl alcohol 15:4).

Example 19

Thin layer sugar-coated tablets were obtained in the same manner as Example 2 with the exception of using a sugar coating liquid obtained by dissolving 120 g of D-mannitol (Mannit P, Towa Chemical Industry Co., Ltd.) and 32 g of polyvinyl alcohol-acrylic acid-methyl methacrylate copolymer (Daido Chemical Corp.) in 608 g of purified water (ratio between D-mannitol and polyvinyl alcohol-acrylic acid-methyl methacrylate copolymer=15:4).

Example 20

Thin layer sugar-coated tablets were obtained in the same manner as Example 2 with the exception of using a sugar coating liquid obtained by dissolving 120 g of erythritol (Nikken Chemical Laboratory Co., Ltd.) and 32 g of completely saponified polyvinyl alcohol (Kyowa Pure Chemical Co., Ltd.) in 608 g of purified water (ratio between D-mannitol and completely saponified polyvinyl alcohol 15:4).

Example 21

Thin layer sugar-coated tablets were obtained in the same manner as Example 2 with the exception of using a sugar coating liquid obtained by dissolving 120 g of erythritol (Nikken Chemical Laboratory Co., Ltd.) and 32 g of polyvinyl alcohol-polyethylene glycol graft copolymer (BASE Corp.) in 608 g of purified water (ratio between D-mannitol and polyvinyl alcohol-polyethylene glycol graft copolymer=15:4).

Example 22

Thin layer sugar-coated tablets were obtained in the same manner as Example 2 with the exception of using a sugar coating liquid obtained by dissolving 120 g of erythritol (Nikken Chemical Laboratory Co., Ltd.) and 32 g of polyvinyl alcohol-acrylic acid-methyl methacrylate copolymer (Daido Chemical Corp.) in 608 g of purified water (ratio between erythritol and polyvinyl alcohol-acrylic acid-methyl methacrylate copolymer=15:4).

[Evaluation of Unpleasant Odor Masking: Case of Using Various Polyvinyl Alcohol-Based Resins]

The thin layer sugar-coated tablets of Examples 18 to 22 were stored for 1 week at 60° C. followed by measurement of the amount of hydrogen sulfide generated in the same manner as Example 2 to evaluate odor masking effects. The results of measuring hydrogen sulfide generation are shown in Table 13.

In Table 13, "Man" indicates D-mannitol, "ERT" indicates erythritol, "completely saponified" indicates completely saponified polyvinyl alcohol, "copolymer" indicates polyvinyl alcohol-acrylic acid-methyl methacrylate copolymer, and "graft polymer" indicates polyvinyl alcohol-polyethylene glycol graft copolymer.

The thin layer sugar-coated tablets of Examples 18 to 22, which used a sugar coating liquid containing mannitol or erythritol and completely saponified polyvinyl alcohol, polyvinyl alcohol-acrylic acid-methyl methacrylate copolymer or polyvinyl alcohol-polyethylene glycol graft copolymer, all demonstrated hydrogen sulfide generation of 5 ppm or less and had high odor masking effects.

TABLE 13

| | Hydrogen Sulfide Generation (ppm) (60° C., 1 week) | | | | |
|---|---|---|---|---|---|
| | Examples | | | | |
| No. | 18 Man Completely saponified | 19 Man Co-polymer | 20 ERT Completely saponified | 21 ERT Graft copolymer | 22 ERT Co-polymer |
| 1 | 0 | 0 | 0 | 2.8 | 1.0 |
| 2 | 0 | 0 | 0 | 3.0 | 1.0 |
| 3 | 0 | 0 | 0 | 4.0 | 1.2 |
| 4 | 0 | 0 | 0 | 2.0 | 0.5 |
| 5 | 0 | 0.5 | 0 | 4.0 | 0.3 |
| 6 | 0 | 0 | 0 | 3.0 | 1.7 |
| 7 | 0 | ≤0.2 | 0 | 5.0 | 2.3 |
| 8 | 0 | 0 | 0 | 2.0 | 0.9 |
| 9 | 0 | 0 | 0 | 2.0 | 0.9 |
| 10 | 0 | 0 | 0 | 3.0 | 0.8 |

[Evaluation of Moisture Resistance: Case of Using Various Polyvinyl Alcohol-Based Resins]

25 tablets each of the thin layer sugar-coated tablets of Examples 18 to 22 were exposed to 25° C. and 75% RH in the same manner as Example 2 followed by followed by evaluating moisture resistance according to change in weight 48 hours later. The results of measuring moisture uptake are shown in Table 14.

The thin layer sugar-coated tablets of Examples 18 to 22, which used a sugar coating liquid containing mannitol or erythritol and completely saponified polyvinyl alcohol, polyvinyl alcohol-acrylic acid-methyl methacrylate copolymer or polyvinyl alcohol-polyethylene glycol graft copolymer, all demonstrated extremely low moisture uptakes of 2% or less and had favorable moisture resistance.

TABLE 14

| | Moisture Uptake (%) | | | | |
|---|---|---|---|---|---|
| | Examples | | | | |
| No. | 18 Man Completely saponified | 19 Man Co-polymer | 20 ERT Completely saponified | 21 ERT Graft copolymer | 22 ERT Co-polymer |
| 1 | 0.49 | 0.26 | 0.51 | 1.96 | 0.33 |
| 2 | 0.50 | 0.26 | 0.51 | 1.94 | 0.31 |
| 3 | 0.50 | 0.27 | 0.47 | 1.92 | 0.33 |

Example 23

90 g of Garlic extract (prepared in-house), 27 g of dried Ginseng extract (Nippon Funmatsu Yakuhin Co., Ltd.), 0.3 g of powdered Oriental Bezoar (Mitsuboshi Pharmaceutical Co., Ltd.), 2.25 g of Civet powder (Matsuura Yakugyo Co., Ltd.), 4.5 g of powdered Deer Velvet Antler (Nippon Funmatsu Yakuhin Co., Ltd.), 3 g of dried Cuscuta Seed extract (Alps Pharmaceutical Ind. Co., Ltd.), 0.3 g of Epimedium (Alps Pharmaceutical Ind. Co., Ltd.), 15 g of liver hydrolysate extract (Nissui Pharmaceutical Co., Ltd.), 3 g of thiamine chloride hydrochloride (Nippon Bulk Yakuhin Co., Ltd.), 3 g of benfotiamine (Kongo Chemical Co., Ltd.), 0.6 g of riboflavin sodium phosphate (DSM Nutrition Japan K.K.), 3 g of pyridoxine hydrochloride (Daiichi Fine Chemical Co., Ltd.), 0.003 g of cyanocobalamin (Sandi-Mends K.K.), 15 g of calcium ascorbate (Takeda Pharmaceutical Co., Ltd.), 6 g of d-α-tocopherol acetate (Riken Vitamin Co., Ltd.), 3 g of nicotinic acid amide (Lonza Japan K.K.), 3 g of calcium pantothenate (Takeda Pharmaceutical Co., Ltd.), 0.06 g of folic acid (DSM Nutrition Japan K.K.), 499 g of crystalline cellulose (Ceolus PH-102, Asahi Kasei Chemicals Corp.) and 30 g of croscarmellose sodium (FMC Co., Ltd.) were kneaded using a dampening machine (PM-5W, Kikusui Seisakusho Ltd.), dried and granulated using a fluidized bed granulator (MP-01, Powrex Corp.). Subsequently, the granules were sized using a sieve (30 mesh) to obtain a sized powder. 8.55 g of silicon dioxide (Maikon F, Tomita Pharmaceutical Co., Ltd.) and 2.85 g of magnesium stearate (Taihei Chemical Industrial Co., Ltd.) were mixed with 673 g of the resulting sized powder in a plastic bag, and the resulting mixed powder was tableted with a rotary tableting machine (Hata Iron Works Co., Ltd.) to a weight of 120 mg, diameter of 7 mm and thickness of 3.8 mm per tablet to obtain uncoated tablets. The composition of the tablets (amounts in 20 tablets) is shown in Table 15.

TABLE 15

| Component | Incorporated Amount |
| --- | --- |
| Garlic extract | 300 mg |
| Dried *Ginseng* extract | 90 mg |
| Powdered Oriental Bezoar | 1 mg |
| Civet powder | 7.5 mg |
| Powdered Deer Velvet Antler | 15 mg |
| Dried *Cuscuta* Seed extract | 10 mg |
| *Epimedium* extract | 1 mg |
| Liver hydrolysate extract | 50 mg |
| Thiamine chloride hydrochloride | 10 mg |
| Benfotiamine | 10 mg |
| Riboflavin sodium phosphate | 2 mg |
| Pyridoxine hydrochloride | 10 mg |
| Cyanocobalamin | 0.01 mg |
| Calcium ascorbate | 50 mg |
| d-α-tocopherol acetate | 20 mg |
| Nicotinic acid amide | 10 mg |
| Calcium pantothenate | 10 mg |
| Folic acid | 0.2 mg |
| Crystalline cellulose (Ceolus PH-102) | 1663.3 mg |
| Croscarmellose sodium | 100 mg |
| Silicon dioxide | 30 mg |
| Magnesium stearate | 10 mg |
| Total | 2400 mg |

A sugar coating liquid obtained by dissolving 120 g of D-mannitol (Mannit P, Towa Chemical Industry Co., Ltd.) and 32 g of partially saponified polyvinyl alcohol (Gohsenol EG-05, Nippon Synthetic Chemical Industry Co., Ltd.) in 608 g of purified water (ratio between D-mannitol and partially saponified polyvinyl alcohol=15:4), was coated onto 100 g of the resulting uncoated tablets at 50% by mass of the uncoated tablets using a coating machine (Doria Coater DRC-200, Powrex Corp.) to obtain sugar-coated tablets.

Example 24

Thin layer sugar-coated tablets were obtained in the same manner as Example 23 with the exception of using a sugar coating liquid obtained by dissolving 120 g of erythritol (Nikken Chemical Laboratory Co., Ltd.) and 32 g of partially saponified polyvinyl alcohol (Gohsenol EG-05, Nippon Synthetic Chemical Industry Co., Ltd.) in 608 g of purified water (ratio between erythritol and partially saponified polyvinyl alcohol=15:4).

Comparative Example 10

Film-coated tablets were obtained by coating a 15% aqueous solution of a polyvinyl alcohol-containing film coating composition (Opadry AMB, Colorcon Japan LLC) onto 100 g of the uncoated tablets of Example 23 using a coating machine (Doria Coater DRC-200, Powrex Corp.) at 5% by mass of the uncoated tablets.

[Evaluation of Unpleasant Odor Masking: Case of Uncoated Tablets Containing Raw Material Having Odor Other than Hydrogen Sulfide]

50 tablets each of the uncoated tablets of Example 23, the film-coated tablets of Comparative Example 10 and thin layer sugar-coated tablets of Examples 23 and 24 were placed in plastic containers followed by sealing the containers. Subsequently, the containers were stored for 1 week at 60° C. and intensity of the odor after opening the containers was evaluated in the form of a sensory evaluation by five panelists. The intensities of the odors were scored to one of four levels shown in Table 16.

<Parameter>

Degree of odor: Intensity of odor as determined by sensory evaluation

TABLE 16

| Degree of odor | Score |
| --- | --- |
| Strong odor (distinct odor after opening container) | 5 |
| Moderate odor (odor detected when wafted with hand after opening container) | 3 |
| Slight odor (slight odor when smelling inside container) | 1 |
| Odorless (no odor even when smelling inside container) | 0 |

<Results>

The results of the sensory evaluation are shown in Table 17. Although the film-coated tablets obtained with the polyvinyl alcohol-containing film coating composition of Comparative Example 10 had a distinct odor derived from the raw materials contained in the uncoated tablets, the thin layer sugar-coated tablets of Examples 23 and 24 had hardly any odor.

TABLE 17

| | Degree of Odor (Score) | | | |
| --- | --- | --- | --- | --- |
| | Uncoated tablets of | Comparative Example | Examples | |
| Subject | Example 23 | 10 | 23 | 24 |
| A | 5 | 3 | 1 | 1 |
| B | 5 | 1 | 0 | 0 |
| C | 3 | 3 | 0 | 0 |
| D | 5 | 3 | 0 | 0 |
| E | 3 | 1 | 0 | 0 |
| Total | 21 | 11 | 1 | 1 |
| Average | 4.2 | 2.2 | 0.2 | 0.2 |

[Evaluation of Moisture Resistance: Case of Uncoated Tablets Containing Raw Materials Having Odor Other than Hydrogen Sulfide]

25 tablets each of the uncoated tablets of Example 23, film-coated tablets of Comparative Example 10 and the sugar-coated tablets of Examples 23 and 24 were exposed to 25° C. and 75% RH in the same manner as Example 2 followed by evaluating moisture resistance according to change in weight 48 hours later.

<Results>

The results of measuring moisture uptake are shown in Table 18. Although the film-coated tablets obtained using the polyvinyl alcohol-containing film coating composition of Comparative Example 10 absorbed moisture to roughly the same degree as that of uncoated tablets, the sugar-coated tablets of Examples 23 and 24 both demonstrated extremely low moisture uptake of 0.5% or less and had favorable moisture resistance.

TABLE 18

| | Moisture Uptake (%) | | | |
|---|---|---|---|---|
| | Uncoated tablets of | Comparative Example | Examples | |
| No. | Example 23 | 10 | 23 | 24 |
| 1 | 8.58 | 8.49 | 0.30 | 0.38 |
| 2 | 8.55 | 8.55 | 0.30 | 0.37 |
| 3 | 8.57 | 8.56 | 0.30 | 0.38 |

Example 25

Thin layer sugar-coated tablets were obtained in the same manner as Example 2 with the exception of using a sugar coating liquid obtained by dissolving 90 g of D-mannitol (Mannit P, Towa Chemical Industry Co., Ltd.), 30 g of erythritol (Nikken Chemical Laboratory Co., Ltd.) and 32 g of partially saponified polyvinyl alcohol (Gohsenol EG-05, Nippon Synthetic Chemical Industry Co., Ltd.) in 608 g of purified water (ratio between D-mannitol, erythritol, and partially saponified polyvinyl alcohol 11.25:3.75:4).

Example 26

Thin layer sugar-coated tablets were obtained in the same manner as Example 2 with the exception of using a sugar coating liquid obtained by dissolving 30 g of D-mannitol (Mannit P, Towa Chemical Industry Co., Ltd.), 90 g of erythritol (Nikken Chemical Laboratory Co., Ltd.) and 32 g of partially saponified polyvinyl alcohol (Gohsenol EG-05, Nippon Synthetic Chemical Industry Co., Ltd.) in 608 g of purified water (ratio between D-mannitol, erythritol and partially saponified polyvinyl alcohol 3.75:11.25:4).

[Evaluation of Unpleasant Odor Masking: Case of Combining Use of D-Mannitol and Erythritol]

The sugar-coated tablets of Examples 25 and 26 were stored for 1 week at 60° C. in the same manner as Example 2 followed by measuring the amount of hydrogen sulfide generated to evaluate odor masking effects. The results of measuring hydrogen sulfide generation are shown in Table 19.

In Table 19, the numbers in parentheses shown below the numbers of the examples represent the weight ratio between D-mannitol, erythritol, and partially saponified polyvinyl alcohol ([D-mannitol content]:[erythritol content]: [partially saponified polyvinyl alcohol content]) of the sugar coating liquid used. The sugar-coated tablets of Examples 25 and 26 demonstrated extremely low generation of hydrogen sulfide of 1 ppm or less and had high odor masking effects.

TABLE 19

| | Hydrogen Sulfide Generation (ppm) | |
|---|---|---|
| | Examples | |
| No. | 25 (11.25:3.75:4) | 26 (3.75:11.25:4) |
| 1 | 0.7 | 0 |
| 2 | 0.2 | 0.2 |
| 3 | 0.7 | 0 |
| 4 | 0.3 | 0 |
| 5 | 0.2 | 0.7 |
| 6 | 0 | 0 |
| 7 | 0.5 | ≦0.2 |
| 8 | 0.2 | 0 |
| 9 | 0 | 0 |
| 10 | ≦0.2 | 0.2 |

[Evaluation of Moisture Resistance: Case of Combining Use of D-Mannitol and Erythritol]

25 tablets each of the sugar-coated tablets of Examples 25 and 26 were exposed to 25° C. and 75% RH in the same manner as Example 2 followed by evaluating moisture resistance according to change in weight 48 hours later.

The results of measuring moisture uptake are shown in Table 20. The sugar-coated tablets of Examples 25 and 26 demonstrated extremely low moisture uptake of 1% or less and had favorable moisture resistance.

TABLE 20

| | Moisture Uptake (%) | |
|---|---|---|
| | Example | |
| No. | 25 (11.25:3.75:4) | 26 (3.75:11.25:4) |
| 1 | 0.99 | 0.52 |
| 2 | 0.98 | 0.51 |
| 3 | 0.98 | 0.52 |

INDUSTRIAL APPLICABILITY

According to the production method of a sugar-coated preparation of the present invention, since a sugar-coated preparation having superior unpleasant odor masking ability and moisture resistance can be produced more easily, the sugar-coated preparation can be used in production fields in which sugar-coated preparations are used, such as pharmaceuticals, quasi drugs, cosmetics, functional foods, health foods and ordinary foods.

The invention claimed is:

1. A sugar-coated preparation including a solid composition containing a pharmacologically active ingredient and a sugar coating layer,
   wherein the sugar coating layer is made of a sugar coating composition consisting essentially of:
   one or more sugar-alcohols selected from the group consisting of mannitol and erythritol; and
   a polyvinyl alcohol-based resin selected from the group consisting of partially saponified polyvinyl alcohols having a degree of saponification of less than 97 mol %, completely saponified polyvinyl alcohols having a degree of saponification of 97 mol % or more, polyvinyl alcohol-polyethylene glycol graft copolymers and polyvinyl alcohol-acrylic acid-methyl methacrylate copolymers, wherein
   the mass ratio between the sugar-alcohol and the polyvinyl alcohol-based resin of the sugar coating composition is 15:4 to 15:20.

2. The sugar-coated preparation according to claim 1, wherein the mass ratio between the sugar-alcohol and the polyvinyl alcohol-based resin of the sugar coating composition is 15:4 to 15:8.

3. The sugar-coated preparation according to claim 1, wherein the sugar coating layer is formed by coating one layer of the sugar coating composition by spraying.

4. The sugar-coated preparation according to claim 1, wherein the sugar-coated preparation is a tablet, granules or grains.

5. A sugar coating composition, consisting essentially of:
   one or more sugar-alcohols selected from the group consisting of mannitol and erythritol; and a polyvinyl alcohol-based resin selected from the group consisting of partially saponified polyvinyl alcohols having a degree of saponification of less than 97 mol %, completely saponified polyvinyl alcohols having a degree of saponification of 97 mol % or more, polyvinyl alcohol-polyethylene glycol graft copolymers and polyvinyl alcohol-acrylic acid-methyl methacrylate copolymers, wherein an amount of the polyvinyl alcohol-based resin is more than 0.27 times the amount of the sugar-alcohol in mass ratio.

6. A sugar-coated preparation coated with the sugar coating composition according to claim 5.

7. The sugar-coated preparation according to claim 6 wherein the sugar-coated preparation is a tablet, granules or grains.

8. The sugar-coated preparation according to claim 2, wherein the sugar coating layer is formed by coating one layer of the sugar coating composition by spraying.

9. The sugar-coated preparation according to claim 2, wherein the sugar-coated preparation is a tablet, granules or grains.

10. The sugar-coated preparation according to claim 3, wherein the sugar-coated preparation is a tablet, granules or grains.

* * * * *